United States Patent [19]
Lehna

[11] Patent Number: 5,343,773
[45] Date of Patent: Sep. 6, 1994

[54] DEVICE FOR GENERATING AND DECOUPLING DIFFERENT MOVEMENTS IN CLEANING AND SEALING STATIONS IN INK PRINTERS

[75] Inventor: Heinz Lehna, Rosenheim, Fed. Rep. of Germany

[73] Assignee: Siemens Aktiengesellschaft, Munich, Fed. Rep. of Germany

[21] Appl. No.: 910,089
[22] PCT Filed: Dec. 4, 1990
[86] PCT No.: PCT/DE90/00939
  § 371 Date: Sep. 10, 1992
  § 102(e) Date: Sep. 10, 1992
[87] PCT Pub. No.: WO91/10568
  PCT Pub. Date: Jul. 25, 1991

[30] Foreign Application Priority Data
  Jan. 9, 1990 [DE] Fed. Rep. of Germany ....... 4000417

[51] Int. Cl.$^5$ ...................... F16H 27/02; F16H 53/06; G01D 15/16
[52] U.S. Cl. .......................... 74/89; 74/54; 74/105; 74/569
[58] Field of Search ............... 74/53, 54, 57, 569, 74/89, 55, 567, 105; 400/120 PH; 346/140 R, 140 PD

[56] References Cited

U.S. PATENT DOCUMENTS

| | | | |
|---|---|---|---|
| 3,802,280 | 4/1974 | Shelmire | 74/89 |
| 3,869,924 | 3/1975 | Beezer | 74/57 X |
| 4,739,340 | 4/1988 | Terasawa | 346/140 PD X |
| 4,796,430 | 1/1989 | Malaker et al. | 74/57 X |
| 4,800,403 | 1/1989 | Accattino et al. | 346/140 R |
| 4,970,534 | 11/1990 | Terasawa et al. | 346/140 PD X |
| 5,142,925 | 9/1992 | Fauvel | 74/54 |

Primary Examiner—Leslie A. Braun
Assistant Examiner—David W. Laub
Attorney, Agent, or Firm—Cohen, Pontani, Lieberman, Pavane

[57] ABSTRACT

A motor-driven cam disk having a radially projecting, eccentrically arranged crank pin which generates a first movement, for example the pumping movement of a bellows pump. A running wheel which is pressed by a spring force against the cam disk in a resilient manner is arranged in the radial direction on the cam disk. The running wheel serves to generate a second movement, for example the swiveling movement of a swivel lever. For this purpose, the motor-driven cam disk has two cam paths which are offset relative to one another in a stepped manner and pass into one another at two locations on the cam disk. The cam disk has a switch tongue to enable the movements generated by the motor-driven cam disk to be decoupled from one another.

7 Claims, 2 Drawing Sheets

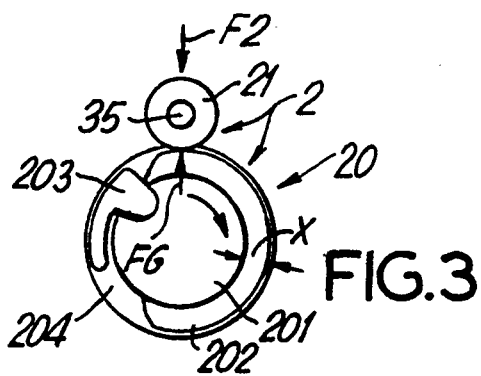
FIG.3
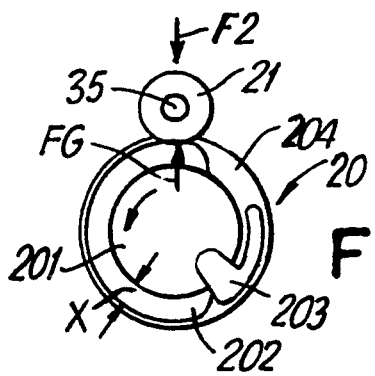
FIG.4
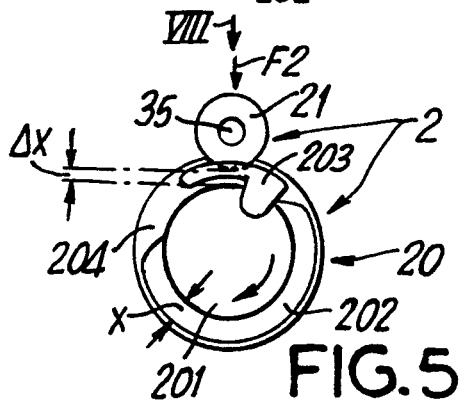
FIG.5
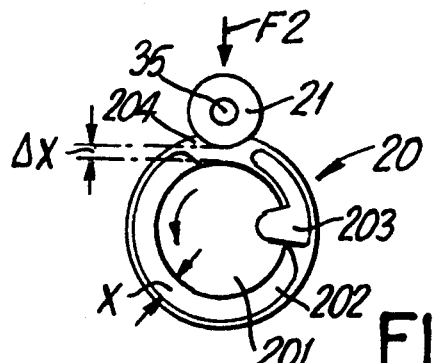
FIG.6
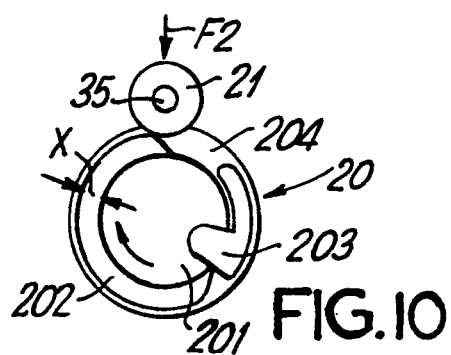
FIG.10
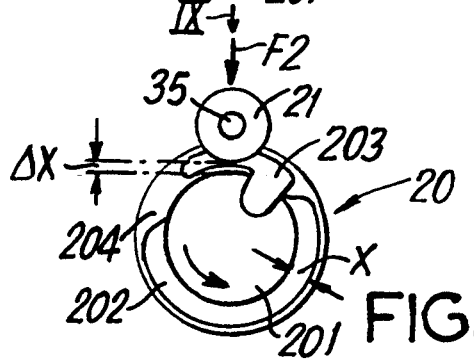
FIG.7
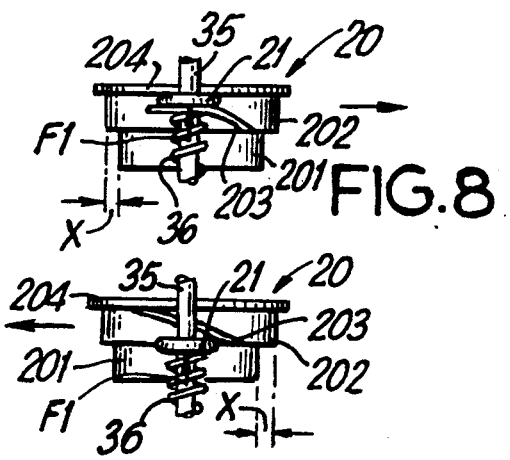
FIG.8
FIG.9
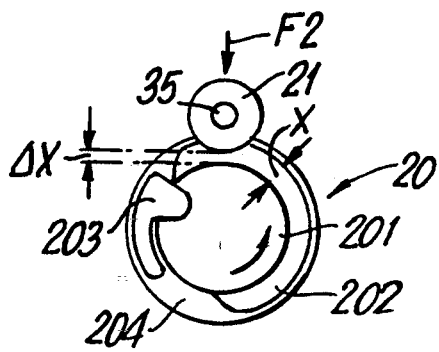
FIG.11

DEVICE FOR GENERATING AND DECOUPLING DIFFERENT MOVEMENTS IN CLEANING AND SEALING STATIONS IN INK PRINTERS

BACKGROUND OF THE INVENTION

1. Field of the Invention

The invention is directed to a device for generating and decoupling different movements in cleaning and sealing stations in ink printers.

2. Description of the Prior Art

Along with a multitude of other terminal units for texts, for example needle, matrix, thermal-transfer and electro-photographic printers, ink printers have assumed increasing importance for the user as a result of the development of increasingly powerful microprocessors. Due to the growing efficiency of text-processing peripheral equipment, the procurement of a printer is often a strategic decision in which performance features such as speed, economy and letter quality take the foreground. Moreover, the performance feature of color printing is growing in importance for various applications. Along with thermal-transfer printing, ink printing offers the optimal prerequisites for this through simple and inexpensive production of colored inks. The ink colors used in an ink printer, for example according to DE-A1-37 36 916, are yellow, cyan, magenta and black. The advantage of ink printers, which consists in the inexpensive and simple production of ink, is offset by the disadvantage that the ink dries in the jet outlet openings of an ink printing head over long printing pauses of the ink printer. To prevent this drying, the ink printer comprises e.g. a cleaning and sealing station or suction regenerating device. Beyond this, the cleaning and sealing station has the object of eliminating soiling of the jet outlet openings of the ink printing head in the ink printer. For this purpose, as indicated by the name cleaning and sealing station, the ink printing heads are cleaned at regular intervals and sealed during longer printing pauses of the ink printer. The demands made on the cleaning and sealing station require steps which prevent the mixing of colors during the cleaning and sealing of the ink printing heads and the destruction of meniscuses in jet outlet openings of the ink printing heads when a suction and covering device is coupled with an ink printing mechanism. The suction and covering device is arranged, for example in a two-part swivel lever which is constructed so as to be laterally displaceable. To enable the coupling of the suction and covering device with the ink printing mechanism and the suction of ink out of the ink printing heads in the coupled state by means of a pump, the required movements of the swivel lever and pump must be generated and it must be possible to decouple these movements from one another.

A cleaning and sealing station or suction regenerating device for ink printing heads which is known from DE-A1-33 16 474, DE-A1-33 16 968, DE-A1-36 04 373, DE-A1-36 11 333, DE-A1-36 33 239, DE-A1-37 26 671, DE-A1-38 10 698 and EP-A1-0 094 220, cleans and rinses jet outlet openings of the ink printing heads in various ways and seals them over longer pauses in printing of the ink printers. The cleaning and sealing station or suction regenerating device is preferably arranged in the ink printer in a parked position outside the operating range of a printer carriage carrying the ink printing heads. As a result of the additional installation space required for this in the ink printer, depending on the external dimensions of the cleaning and sealing station or suction regenerating device, the ink printer is wider and accordingly less convenient.

The manner in which a suction and covering device is arranged in the cleaning and sealing station so as to be movable forward and backward is known, moreover, from DE-A1-36 11 333. The suction and covering device need only be movable forward and backward because the printer carriage with the ink printing heads can be accurately positioned relative to the cleaning and sealing station by means of the special park position of the cleaning and sealing station. For this purpose, a motor is provided in the cleaning and sealing station which drives a pump lever and the suction and covering device, which is supported so as to slide, via a costly gear unit and accordingly initiates the coupling and suction process.

SUMMARY OF THE INVENTION

The object of the present invention is the construction of a device for generating and decoupling different movements in cleaning and sealing stations in ink printers in an inexpensive and simple manner. By means of this device, a suction and cover cap of the cleaning and sealing station for cleaning ink printing heads can be moved toward a jet plate of the ink printing heads and moved away from the jet plate again and a suction device (bellows pump) can be actuated when the suction and cover cap is docked or parked at the jet plate.

This object is met by a device for generating and decoupling different movements. The device having a motor-driven cam disk that has two paths which are offset relative to one another in a stepped manner and merge at two places on the cam disk. A crank pin is eccentrically arranged on the cam disk to generate a first movement. The device further has a running wheel that is guided by the cam paths to generate a second movement, and a switch tongue that decouples the second movement from the first movement by controlling the path of the running wheel.

BRIEF DESCRIPTION OF THE DRAWINGS

Embodiment examples of the invention are explained with reference to the drawings in FIGS. 1 to 11:

FIGS. 3 to 11 are diagrams showing various states, depending on the rotating direction, of a switch coupling for generating and decoupling the various movements in the cleaning and sealing station.

DETAILED DESCRIPTION OF THE PREFERRED EMBODIMENTS

Figure 1:
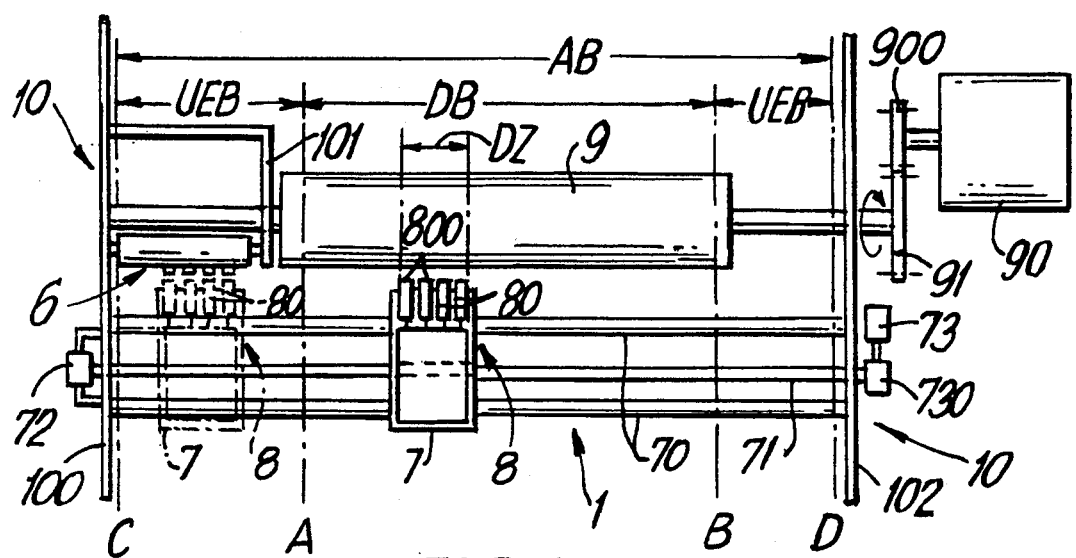
FIG. 1 shows a top view of an ink printer.

FIG. 1 shows a top view of a basic construction of an ink printer 1. It is characteristic for the construction of the ink printer 1 that an ink printing mechanism 8 is arranged on a printer carriage 7 and is movable parallel to a printing support in the form of a platen 9 which is rotatably supported in two housing walls 100, 102 of a supporting framework 10. The platen 9, which is driven in the rotating direction shown in the drawing via a gear unit 91 by a drive device 90 comprising a first drive pinion 900, transports a sheet-like recording medium, which extends e.g. over a printing area DB, in a print zone DZ formed by the ink printing mechanism 8 and the platen 9. When, as in the present case, the ink printer 1 is constructed as a four-color printer, the ink printing mechanism 8 comprises four adjacently arranged ink printing heads 80 with jet outlet faces 800 facing the recording medium to enable a printing of the recording medium. The four available colored inks are yellow, magenta, cyan and black. The colored inks can be assigned to the four different ink printing heads 80 as required. However, for reasons relating to the cleaning of the ink printing heads 80, it is recommended that the colors be assigned to the ink printing heads 80 in the aforementioned sequence from right to left.

The area of the sheet-like recording medium located opposite the ink printing heads 80 is designated as the print zone DZ. In order to print on the sheet-like recording medium over the entire region of the printing area DB, the printer carriage 7 is moved in a reciprocating manner on two parallel guide bars 70 fastened in the housing walls 100, 102. The reciprocating movement of the printer carriage 7 is effected by means of a flexible traction means 71 which is looped in a positive-locking manner around a deflecting roller 72 and a second drive pinion 730 of an electric motor 73. Such a drive of the printer carriage is known from DE-GM 89 06 727.

In order to print on the recording medium guided along the platen 9 in the printing area DB, the printer carriage 7 along with the ink printing mechanism 8 is moved back and forth between the positions defining the printing area DB. Both unidirectional and bidirectional printing operations are possible. In the unidirectional printing operation the recording medium is printed on line by line in only one movement direction. In the bidirectional printing operation—which allows a substantially greater printing speed—the recording medium is imprinted line by line in the printing area DB in both movement directions of the ink printing mechanism 8 (ink printing head).

At the start of printing, regardless of the type of operation, the printer carriage 7 which is located in a rest position C outside the printing area DB is first accelerated to position A so that it achieves the speed relative to the recording medium required for continuous printing. Position A thus defines the first possible print position. The printer carriage 7 is then moved in the actual printing area DB for printing at constant speed until it has reached position B which determines the last possible print position of the printing area DB. After passing position B, the printer carriage 7 is braked until position D and brought to a stop and then the recording medium is moved further by one printing line via the platen 7. To print the following line the printer carriage is accelerated in the opposite direction out of position D into position B which now determines the first print position of the following line to be printed. After reaching the printing speed in position B, the following line can be printed between positions B and A. When the printer carriage 7 reaches the last possible print position A, it is braked again until position C. A new line advance with the printing of a new line is now effected. The recording medium is now imprinted line by line in the described manner.

In unidirectional operation it is advantageous to move the printer carriage from position B into position C with fast return.

The distances CA and BD are designated in the following as overshoot areas UEB which, with the printing area DB, determine an operating area AB for the ink printing mechanism 8. Their minimum length is determined by the physically necessary acceleration and braking distances while taking into account mechanical tolerances. In the embodiment example described with reference to FIG. 1, the overshoot area UEB is approximately 40 mm long.

During the printing operation, dirt can accumulate at the ink printing heads 80 as a result of paper dust. For this reason the ink printing heads 80 must be cleaned from time to time. The ink printing heads 80 are rinsed in that ink is sucked out of the ink printing heads 80 via the jet outlet openings. The rinsing of the ink printing heads 80 also simultaneously prevents ink from drying in jet outlet openings of ink printing heads 80 which were not used during the printing operation. A cleaning and sealing station 6 is provided in the ink printer 1 for this purpose. The cleaning and sealing station 6 is arranged in an overshoot area UEB of the printer carriage 7. This overshoot area UEB can be on the left side as well as on the right side. The left-hand overshoot area has proven advantageous.

To clean the ink printing heads 80, the printer carriage 7 is moved into the overshoot area UEB until contacting the housing wall 100 of the supporting framework 10. The housing wall 100 thus forms a common index edge for the cleaning and sealing station 6 and the printer carriage 7, which is important for the cleaning process. The cleaning process will be discussed in detail with reference to the description of FIGS. 2 to 11.

Figure 2:
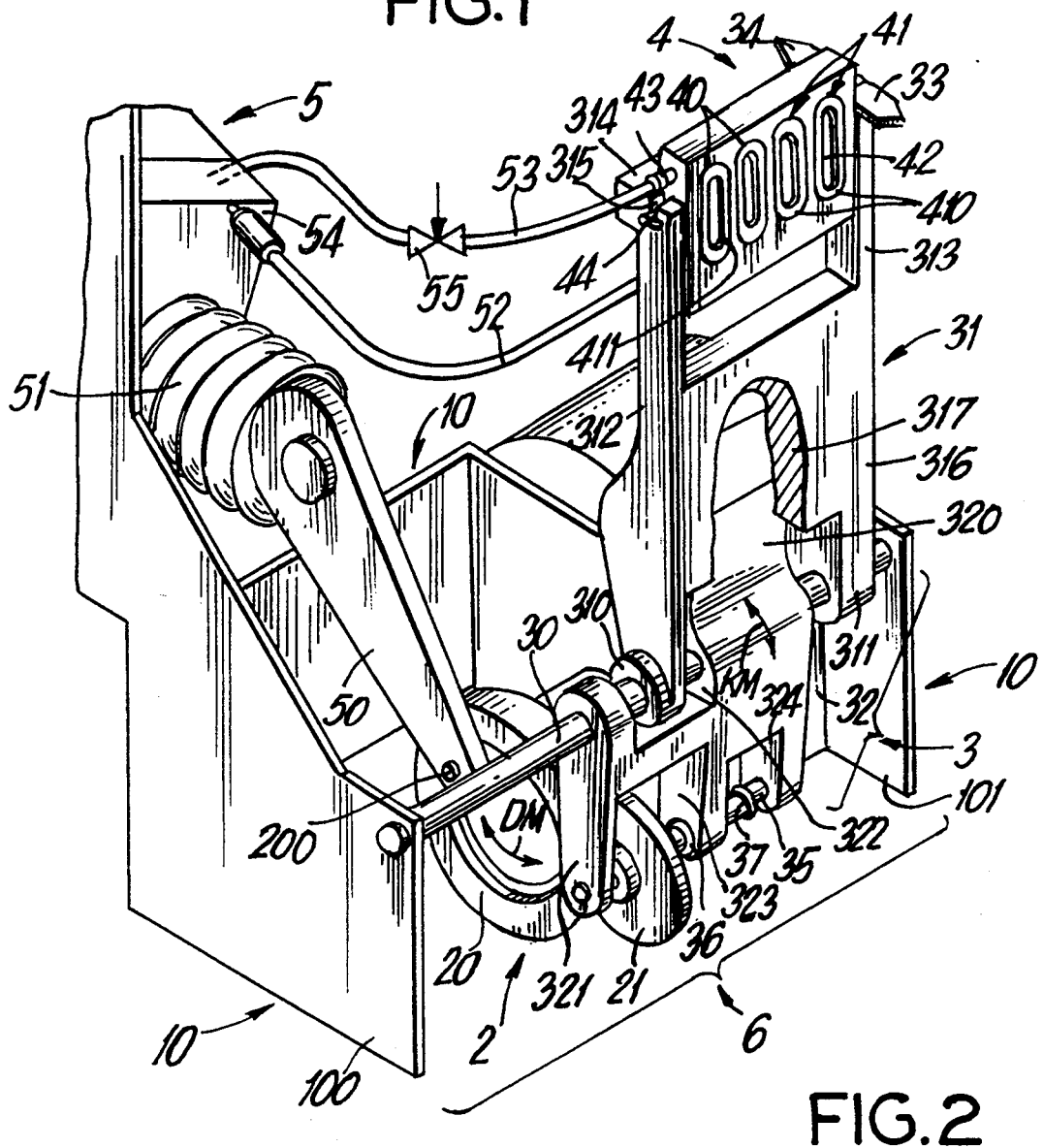
FIG. 2 shows a perspective view of a cleaning and sealing station.

FIG. 2 shows a perspective view of the construction of the cleaning and sealing station 6, designated in the following as RD station. The RD station 6 is conceived as an autonomous construction unit functioning independently from the ink printer 1. It can be inserted in the ink printer as a self-contained construction unit. This has the advantage that the RD station 6 can be used as OEM (Original Equipment Manufacturing) product in different ink printers. Servicing of the ink printing heads 80 which is necessary for a trouble-free operation of the ink printer 1 can be carried out with them. This servicing includes: cleaning the ink printing head 80, including its jet outlet openings, at predetermined time intervals so as to prevent a drying and soiling of the jet outlet openings; sucking out ink contained in the ink printing head 80 during disturbances, for example so as to remove air which has penetrated, and—in the rest state of the ink printer 1—covering the jet outlet openings so as to protect them from drying and soiling, e.g. as a result of paper dust. Moreover, ink must be prevented from running out of the jet outlet openings when transporting and storing the ink printer 1.

Since the RD station 6 according to FIG. 1 is arranged in the ink printer 1 within the overshoot area UEB for the printer carriage 7 carrying the ink printing mechanism 8, which overshoot area UEB results from the printing operation of the ink printer 1, a narrower construction of the ink printer 1 results.

During the printing operation, when the printer carriage 7 stops temporarily in the overshoot area UEB as a result of the acceleration and braking processes, the RD station 6 may not block the overshoot distance of the printer carriage 7 between position A and position C according to FIG. 1.

In servicing operation, when the jet outlet openings of the ink printing mechanism 8 are to be cleaned, the RD station 6 must be parked at the ink printing mechanism 8 so as to be accurately positioned and the ink must be sucked out of the jet outlet openings. "Parking" is understood as a coupling of the RD station 6 with the ink printing mechanism 8.

In the rest state, during the transporting and storage of the ink printer 1, the jet outlet openings must be protected from drying. Further, no ink may run out. Therefore it is necessary to park the RD station 6 at the ink printing mechanism 8 so as to be accurately positioned and accordingly to seal the jet outlet openings.

The RD station 6 contains a switch coupling 2, a swivel lever 3, a suction and cover cap 4, designated in the following as SA cap, and a bellows pump 5. The switch coupling 2 comprises a cam disk 20 and a running wheel 21 which rolls on the cam disk 20. The cam disk 20 is fastened in a positive-locking manner on a drive shaft of an additional electric motor, not shown in FIG. 2, to receive a torque DM. The electric motor is preferably a D.C. motor.

Further, the cam disk 20 comprises an eccentrically arranged, projecting crank pin 200 on the end face side remote of the electric motor, which crank pin 200 is connected with a bellows 51 of the bellows pump 5 via a rod linkage 50. The bellows 51 is alternately drawn out and pressed together via the rod linkage 50 due to the rotation of the cam disk 20 with the eccentric crank pin 200. The resulting pump action of the bellows pump 5 is used in the present RD station 6, for example, to pump the ink out of the jet outlet openings of the ink printing heads 80 in FIG. 1. The bellows pump 5 is connected with the SA cap 4 via a tube 52 as well as an air hose 53. However, with the RD station 6 it is also possible to suck other liquids out of diverse injection devices and to dispose of them.

Four equally sized and identically formed recesses (suction openings, hollow spaces) 40 are arranged in the SA cap 4 for pumping the ink out of the ink printing heads 80 of the ink printer 1. These recesses 40 are connected via the tube 52 (suction duct) with a disposal tank 54 fastened at the bellows pump 5 on the one hand and with the surrounding air via the air hose 53 (pressure compensating duct) on the other hand. The air hose 53 comprises, for example, a controllable venting valve 55 which, for example, is coupled with the bellows pump 5. The air hose 53 is drawn over a venting connection piece 43 which projects out of the SA cap 4 at the side. The ink can also be sucked out of the jet outlet openings with a hose, piston and diaphragm pump as an alternative to the bellows pump 5.

The number of recesses 40 contained in the SA cap 4 of the RD station 6 depends on the number of ink printing heads used. If, for example, a four-color printed image is to be produced with the ink printer 1, as in the present case, the servicing of the ink printer 1 must also be designed for the disposal of the required four ink printing heads. To prevent a mixing of inks when sucking ink out of the jet outlet openings of the ink printing heads, the number of recesses 40 or suction openings is identical to the number of utilized colored inks assigned to the ink printing heads.

A trough-shaped rubber insert 41 in the form of an elastic cap is arranged in the suction openings 40 on the side of the SA cap 4 facing the ink printing mechanism 8. This cap comprises a liquid-absorbing lining 42. As was already mentioned, the SA cap 4 is parked at the ink printing mechanism 8 for pumping the ink out of the ink printing heads 80, wherein the rubber inserts 41 lie over the jet outlet openings. The parking of the SA cap 4 refers in the following to a lateral displacement and swiveling of the SA cap 4. A sealing lip 410 enclosing a trough opening 411 of the rubber insert 41 is arranged on the trough-shaped rubber insert 41 so that the ink can be pumped out via the suction openings 40 and the tube 52 without difficulty. The sealing lip 410 is pressed against the ink printing mechanism 8 when the SA cap 4 is parked and in so doing the jet outlet openings of the ink printing heads 80 are hermetically sealed.

The parking of the SA cap 4 is effected by the swivel lever 3 which is supported so as to be displaceable and swivelable on a first axle 30 clamped between the housing wall 100 and another housing wall 101 of the supporting framework 10. Friction influences must be kept as low as possible so that the displacement and swiveling of the swivel lever 3 can be carried out with a minimum expenditure of force.

The swiveling process is triggered in that the torque DM generated by the electric motor is transformed via the switch coupling 20 into a tilting moment KM acting on the swivel lever 3. The swivel lever 3 is spring-mounted at the cam disk 20 via the running wheel 21 for transforming the torque DM. In order to minimize the forces occurring in the spring mounting, the swivel lever 3 is constructed in two parts and the inherent weight of the swivel lever 3 which is partially responsible for the friction influences is accordingly also divided. But the reason for the two-part construction of the swivel lever 3 substantially consists in that a lateral displacement of the swivel lever 3 can be required for an accurately positioned parking. In a one-part construction this would lead to a displacement of the running wheel 21 on the cam disk 20. In a one-part construction the running surface for the running wheel 21 on the cam disk 20 would have to be designed for a maximum lateral displacement during parking.

An upper lever part 31 of the swivel lever 3 supporting the SA cap 4 is arranged on the axle 30 so as to be swivelable and displaceable via two swivel arms 310, 311. The upper lever part 31 of the swivel arm 3 further comprises two oppositely located supporting arms 312, 313 which are connected with one another on the side remote of the ink printing mechanism 8 via a U-shaped cross strut 314. In a first embodiment form for the support of the SA cap 4 a T-shaped recess 315 is inserted in the legs of the U-shaped cross strut 314. This serves for the freely movable support of bearing pins 44 of the SA cap 4. The bearing pins 44 are pressed into the T-shaped recess 315 for the support of the SA cap 4. In addition, the upper lever part 31 comprises a rectangular center part 316 between the swivel arms 310, 311 and the supporting arms 312, 313 in which a pocket-shaped formed out portion 317 is arranged.

A positioning device is provided so that the SA cap 4 can also be parked at the ink printing mechanism 8 so as to be accurately positioned. This positioning device comprises two oppositely located centering fingers 34 which taper off in the swiveling direction of the swivel lever 3 and are arranged on the side of the supporting arm 313 on the leg of the U-shaped cross strut 314. During the swiveling of the swivel lever 3, a first centering finger 33 automatically seeks out a first centering window, not shown in FIG. 2, which is inserted in the ink printing mechanism 8 and thus positions the RD station 6 relative to the ink printing mechanism 8. The swivel lever 3 can be displaced laterally along with the RD station 6 for positioning.

To park the SA cap 4, the tilting moment KM is transmitted to the upper lever part 31 of the swivel lever 3 via a lower lever part 32 of the swivel lever 3.

As in the case of the upper lever part 31, the lower lever part 32 is arranged on the axle 30 so as to be swivelable. A lever arm 320 and a secondary arm 321 which are penetrated by the axle 30 in the center and at the foot, respectively, are characteristic of the lower lever part 32. A first cut out portion 322 in which the swivel arm 310 of the upper lever part 31 is arranged is provided between the lever arm 320 and the secondary arm 321 in the region of the axle 30. The dimensions of the cut out portion 322 are selected in such a way that the upper lever part 31 can be displaced laterally if necessary independently of the lower lever part 32. Moreover, a second cut out portion 323 in which the running wheel 21 is supported on a second axle 35 so as to be axially movable and rotatable is provided between the lever arm 320 and the secondary arm 321. Further, a first spring 36 which acts against the axial movability of the running wheel 21 with a first spring force F1 is arranged on the axle 35 inside the cut out portion 323. Moreover, the axle 35 penetrates a third cut out portion 324 which is inserted at the foot of the lever arm 320. A second spring 37 with a spring force F2 is mounted at the axle 35 inside this third cut out portion 324 and is connected with the supporting framework 10 of the ink printer 1 for the swiveling process of the swivel lever 3, although this is not shown in FIG. 1. The running wheel 21 is pressed against the cam disk 20 by means of the second spring force F2 of the spring 37. The swiveling movement of the swivel lever 3 required for parking the SA cap 4 is transmitted to the upper lever part 31 by the lever arm 320 of the lower lever part 32. The lever arm 320 engages with slight play in the swiveling direction of the swivel lever 3 in the pocket-shaped formed out portion 317 of the upper lever part 31 between the swivel arms 310, 311 in the manner of a sliding block. To enable the displacement of the upper lever part 31 on the axle 30, the pocket-shaped formed out portion 317 of the upper lever part 31 is wider than the lever arm 320 of the lower lever part 32 by the amount required for the lateral displacement of the upper lever part 31 and accordingly of the SA cap 4.

FIGS. 3 to 7 and FIGS. 10 and 11 show side views of the construction and manner of operation of the switch coupling 2 with reference to states of the switch coupling 2 for different rotating directions of the cam disk 20, which states depend on the angle of rotation. The two rotating directions of the cam disk 20 are made use of in order to realize the types of operation of the RD station 6 mentioned in the description of FIG. 2. In the right-hand rotation of the cam disk 20 according to FIGS. 3, 5 and 10 the SA cap 4 which is integrated in the swivel lever 5 is parked at the ink printing mechanism 8 (FIG. 3) and lifted from the ink printing mechanism 8 again (FIG. 10) in a constantly changing manner. In the left-hand rotation of the cam disk 20 according to FIGS. 4, 6, 7 and 11 the swivel lever 3 is parked at the ink printing mechanism (FIG. 4) and the ink is sucked out of the jet outlet openings of the ink printing head by means of the bellows pump 5 (FIGS. 6, 7, 11) until the rotating direction is changed again.

For the swiveling and suction process, the cam disk 20 has two radially extending cam paths 201, 202 which are offset relative to one another by a stepped offset x. The outer cam path 202 according to FIGS. 3, 4 and 10, which triggers movement, serves as a running surface for the running wheel 21 rolling on the cam disk 20. In order to execute a stroke required for parking the SA cap 4 at the ink printing mechanism 8 and a stroke for lifting the SA cap 4 from the ink printing mechanism 8, the full stepped offset x between the cam paths 201, 202 is effective for example for two thirds of the circumference on the cam disk 20. The position of the running wheel 21 is displaced relative to the cam disk 20 accompanied by spring force F2 or against spring force F2, respectively, by the amount needed for the stroke in that the movement-triggering outer cam path 202 adapts itself at these locations to an inner cam path 201 constructed as an idling path.

FIGS. 3 and 4 show a possible starting state of the switch coupling 2 in which the running wheel 21 rests on the outer cam path 202 of the cam disk 20 and the SA cap 4 according to FIG. 2, which is integrated in the swivel lever 3, is accordingly in the state in which it is lifted from the ink printing mechanism 8. An equilibrium force FG compensating for the spring force F2 is received by the rotatably supported cam disk 20. The running wheel 21, the swivel lever 3 and the SA cap 4 form a double-armed mechanical lever arrangement in which the spring force F2 acting on the lever arrangement is compensated for either via the running wheel 20 or the SA cap 4. If the cam disk 20 is now rotated in the direction of the arrow shown in the drawing to the right according to FIG. 3 or to the left according to FIG. 4, the running wheel 21 leaves the outer cam path 202 of the cam disk 20 under the influence of spring force F2 in both cases. The resulting displacement of position of the running wheel 21 causes the parking of the SA cap 4 at the ink printing mechanism 8 according to FIG. 2 in that the swivel lever 3 is swiveled by the stroke.

Depending on the state of the ink printer 1, for example printing or servicing operation or rest state, either the pump process, for example during the left-hand rotation of the cam disk 20, or the lifting of the SA cap 4 must be effected for the given rotating direction of the cam disk 20. A switch tongue 203 working according to the coupling principle is provided for this purpose. This switch tongue 203 is arranged in the region of the cam disk 20 outside the stepped offset x. It brushes over the inner cam path 201, is securely connected at one end with the cam disk 20 and contacts a rim 204 of the cam disk 20 in a resilient manner at the other end. The switch tongue 203 is dimensioned in such a way and arranged on the cam disk 20 in such a way that the running wheel 21 does not complete any additional displacement of position during the left-hand rotation of the cam disk 20. The running wheel 21 thus idles relative to the moved cam disk 20 and can execute two displacements in position per revolution during the left-hand rotation of the cam disk 20.

The correct selection of the rotating position depending on the type of operation of the ink printer 1 is carried out by a control device which, like the RD station 6, is a component part of the ink printer 1. The control device is coupled with the electric motor. To control the electric motor, the control device contains e.g. a microprocessor which changes the polarity of a supply voltage connected to the electric motor via a generally known electronic circuit arrangement and accordingly changes the rotating direction of the electric motor. In addition to the electric motor of the RD station 6, the control device also controls the electric motor 73 and the drive device 90 according to FIG. 1. The control device is constructed in a conventional manner in general.

FIGS. 5, 6 and 7 show a state of the switch coupling 2 in which the running wheel 21 has left the outer cam path 202 and the SA cap 4 is accordingly parked at the ink printing mechanism 8. It is characteristic for this state in FIGS. 5, 6 and 7 that the running wheel 21 rests neither on the outer cam path 202 nor on the inner cam path 201 of the cam disk 20 in the parked state of the SA cap 4. When the running wheel 21 leaves the outer cam path 202, the mechanical lever arrangement strives under the influence of the spring force F2 to regain contact. This is achieved in that the equilibrium force FG compensating for the spring force F2 is now applied by the ink printing mechanism 8 in contrast to FIGS. 3 and 4 where the equilibrium force FG compensating for the spring force F2 was applied by the rotatably supported cam disk 20. This means that the stroke to be executed by the swivel lever 3 for parking the SA cap 4 at the ink printing mechanism 8 is smaller than the stepped offset x between the cam paths 201, 202 of the cam disk 20. Accordingly, there is an air gap $\Delta x$ by which the running wheel 21 is lifted from the cam path 201 of the cam disk 20. As a result of the air gap $\Delta x$, there is no additional frictional influence during the change of path of the running wheel 21 according to FIGS. 6 and 7. Consequently, the spring force F1 which presses the running wheel 21 against the rim 204 of the cam disk 20 can be small. A typical stroke value for the RD station 6 lies between 6 and 10 mm, for example. While the running wheel 21 according to FIG. 5 is moved relative to the cam disk 20 between the rim 204 and the switch tongue 203, the running wheel 21 according to FIGS. 6 and 7 is guided past the switch tongue 203 relative to the cam disk 20.

FIGS. 8 and 9 show a top view of the state of the switch coupling 2 according to FIG. 5 and FIG. 7. This clearly shows that the running wheel 21 which is pressed against the rim 204 of the cam disk 20 on the axle 35 by the spring 36 with spring force F1 is moved through between the switch tongue 203 and the rim 204 relative to the cam disk 20 during the right-hand rotation of the cam disk 20 in FIG. 8 and is guided past the switch tongue 203 relative to the cam disk 20 during the left-hand rotation of the cam disk 20 in FIG. 9.

During the relative movement of the running wheel 21 according to FIG. 8, the end of the switch tongue 203 pressing against the rim 204 in a resilient manner is pressed away from the running wheel 21.

During the relative movement of the running wheel 21 according to FIG. 9, the running wheel 21 is displaced on the axle 35 and in so doing the spring 36 is compressed. The spring 36 is compressed by the running wheel 21 until the running wheel 21 has passed the switch tongue 203.

FIG. 10 shows how the running wheel 21 arrives on the outer cam path 202 again during continued right-hand rotation of the cam disk 20 against the spring force F2 and how the SA cap 4 is accordingly lifted from the ink printing mechanism 8. During continued right-hand rotation of the cam disk 20, the state of the switch coupling 2 shown in FIG. 3 is reached again and the parking or lifting of the SA cap 4 is started over again.

FIG. 11 shows how the running wheel 21 is pressed against the stepped offset x of the mutually offset cam paths 201, 202 by means of the spring force F1 during further left-hand rotation of the cam disk 20 after passing the switch tongue 203 in FIGS. 7 and 9. During a further left-hand rotation of the cam disk 20, the state of the switch coupling 2 shown in FIG. 6 is achieved again and the ink is pumped out of the jet outlet openings of the ink printing heads 80 again.

I claim:

1. A device for generating and decoupling different movements in cleaning and sealing stations in ink printers, comprising:
    a motor-driven cam disk having two directions of rotation and a projecting, eccentrically arranged crank pin for generating a first movement,
    the motor-driven cam disk further having first and second cam paths which are offset relative to one another in a stepped manner and merge into one another at two locations on the cam disk;
    a running wheel guided by the cam paths and arranged in a resilient manner on the cam disk by a spring force for generating a second movement in a radial direction relative to the cam disk; and
    a switch tongue arranged on the cam disk so as to decouple the second movement from the first movement in one of the directions of rotation of the cam disk by controlling a rotating path of the running wheel around the cam disk as a function of the rotating direction of the motor-driven cam disk.

2. A device according to claim 1, wherein the switch tongue is a self-controlling switching tongue.

3. A device according to claim 1, wherein the switch tongue is arranged between the two locations on the cam disk where the first cam path merges into the second cam path.

4. A device according to claim 1, wherein the cam disk has a rim, the switch tongue having one end fastened to the cam disk at one of the two locations where the first cam path merges into the second cam path and an opposite end that abuts the rim of the cam disk in a resilient manner so as to brush over the two cam paths.

5. A device according to claim 1, and further comprising spring means imparting an axial spring force against the running wheel so that rotation of the cam disk causes the running wheel to act against the axial spring force.

6. A device according to claim 1 or 5, wherein the running wheel is provided so as to alternately rest on the first cam path under the influence of the switch tongue and lift from the second cam path to form an air gap from the second cam path.

7. A device according to claim 1 or 5, wherein the running wheel is lifted from the second cam path to form an air gap from the cam path when the second movement is decoupled from the first movement.

* * * * *